US008236164B2

(12) United States Patent
Gustafsson et al.

(10) Patent No.: US 8,236,164 B2
(45) Date of Patent: Aug. 7, 2012

(54) MOISTURE SENSOR

(75) Inventors: Göran Gustafsson, Linnköping (SE); Xavier Crispin, Kimstad (SE); Magnus Berggren, Vreta Kloster (SE); Oscar Larsson, Norrköping (SE); Xiaodong Wang, Norrköping (SE)

(73) Assignee: Acreo AB, Kista (SE)

( * ) Notice: Subject to any disclaimer, the term of this patent is extended or adjusted under 35 U.S.C. 154(b) by 86 days.

(21) Appl. No.: 12/805,039

(22) Filed: Jul. 8, 2010

(65) Prior Publication Data
US 2011/0011179 A1 Jan. 20, 2011

Related U.S. Application Data

(60) Provisional application No. 61/213,793, filed on Jul. 16, 2009.

(30) Foreign Application Priority Data

Jul. 16, 2009 (EP) ..................................... 09165618

(51) Int. Cl.
*G01N 7/04* (2006.01)
(52) U.S. Cl. ....... 205/788; 204/430; 340/602; 73/29.01; 324/664
(58) Field of Classification Search .................. 205/788; 204/430; 340/602; 73/29.01; 324/664
See application file for complete search history.

(56) References Cited

U.S. PATENT DOCUMENTS

| 4,549,134 | A | * | 10/1985 | Weiss ............................. 324/664 |
| 7,551,058 | B1 | | 6/2009 | Johnson et al. |
| 2004/0036484 | A1 | | 2/2004 | Tamai |
| 2006/0174693 | A1 | | 8/2006 | Chen et al. |

FOREIGN PATENT DOCUMENTS

JP 59-173742 10/1984

OTHER PUBLICATIONS

Pi-Guey Su et al., "Novel flexible resistive-type humidity sensor", Sensors and Actuators B, Elsevier Sequoia S.A., Lausanne, Switzerland, vol. 123, No. 2, May 6, 2007, pp. 1071-1076.
Jukka Voutilainen, "Methods and Instrumentation for Measuring Moisture in Building Structures", Dissertation University of Helsinki, Mar. 18, 2005, <http://lib.tkk.fi/Diss/2005/isbn9512275236/isbn9512275236.pdf>.
Andrew DeHennis et al., "A Wireless Microsystem for the Remote Sensing of Pressure, Temperature, and Relative Humidity", Journal of Microelectromechanical Systems, Piscataway, New Jersey, vol. 14, No. 1, Feb. 1, 2005, pp. 12-22.
Timothy Harpster et al., "A passive wireless integrated humidity sensor", Sensors and Actuators A, Elsevier Sequoia S.A., Lausanne, Switzerland, vol. 95, No. 2-3, Jan. 1, 2002, pp. 100-107.

* cited by examiner

*Primary Examiner* — Kaj K Olsen
(74) *Attorney, Agent, or Firm* — Harness, Dickey & Pierce, P.L.C.

(57) ABSTRACT

A moisture sensor, for measuring moisture in a building without leaving visible scars to the building surface, is provided. The moisture sensor includes a flexible carrier carrying an antenna for receiving EM-radiation between 9 kHz and 11 MHz and a resonant circuit including a moisture reactive element. The moisture reactive element includes a hygroscopic electrolyte arranged between a first and a second electrode, wherein the electrolyte in the presence of moisture forms mobile ions and provides a complex impedance at least in response to the alternating voltage, which complex impedance varies with the moisture content of the electrolyte.

20 Claims, 7 Drawing Sheets

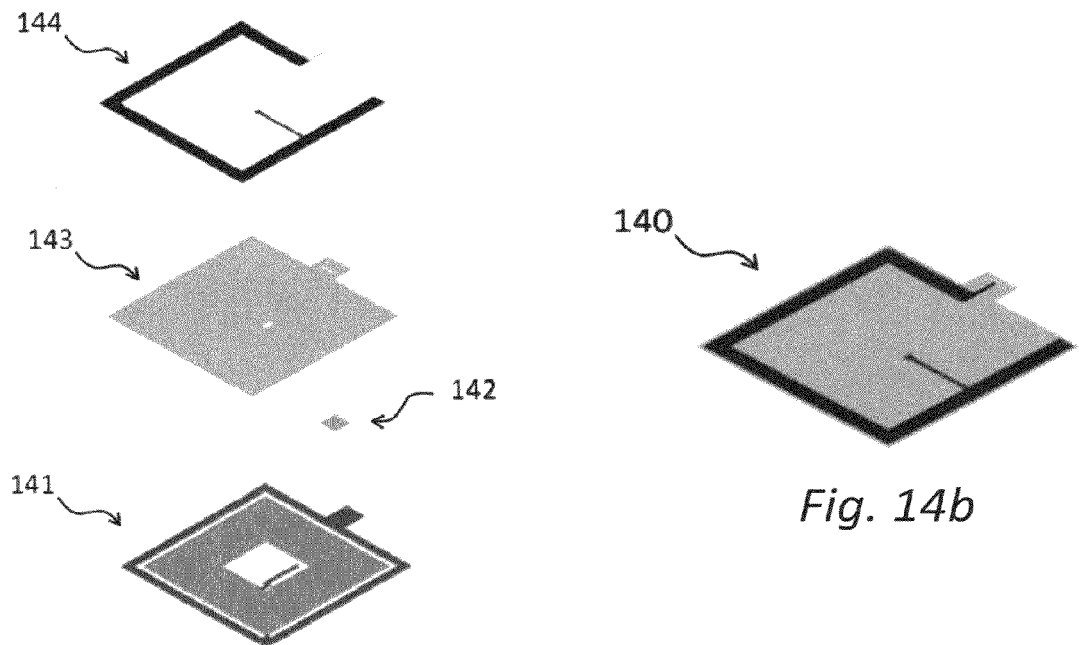
*Fig. 14a*
*Fig. 14b*
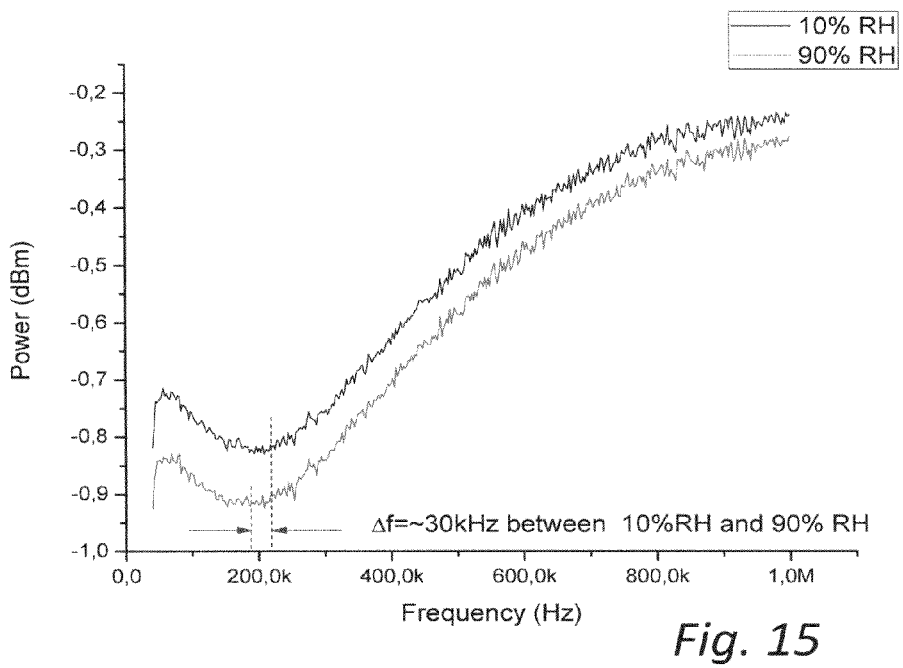
*Fig. 15*

MOISTURE SENSOR

PRIORITY STATEMENT

The present application hereby claims priority under 35 U.S.C. §119 on European patent application number 09165618.1 filed Jul. 16, 2009 and hereby claims priority under 35 U.S.C. §119(e) on U.S. provisional patent application No. 61/213,793 filed Jul. 16, 2009, the entire contents of each of which are hereby incorporated herein by reference.

TECHNICAL FIELD

The invention relates to the field of moisture sensors for buildings, and more specifically to moisture sensors for measuring moisture in building structures such as walls, floors and ceilings.

BACKGROUND OF THE INVENTION

The presence of moisture in e.g. bathroom floors, is a grave concern for many house owners as well as builders and contractors, as a neglected moisture ingress may lead to mould affected areas and eventually unhealthy indoor conditions.

Today the amount of moisture in a building structure, e.g. a building wall, floor or ceiling, is measured by making a hole in the surface and inserting a portion of a handheld moisture measuring instrument into the hole. The moisture level is thereafter read from a display.

This method has the disadvantage of permanently damaging the building surface, requiring a craftsman to conceal the damage, and leaving visually detectable scars on the building structure surface if not mended properly. Furthermore, known moisture devices and methods are further disadvantageous in terms of operation, handling, and functionality.

In "Novel flexible resistive type humidity sensor", Sensors and actuators B, Elsevier Sequoia S. A., Lausanne, CH, vol 123, no 2, 6 May 2007, pages 1071-1076, Su et al. describe a resistive type humidity sensor. The sensor is formed on a polyester substrate provided with gold electrodes for connection of measurement devices.

In "Methods and Instruments for Measuring Moisture in Building Structures, Dissertation University of Helsinki, 18 Mar. 2005 (2005-03-18), XP007909926 ISBN: 978-951-22-7522-9, Voutilainen J. further describes methods and devices for measuring moisture in building.

SUMMARY OF THE INVENTION

In order to eliminate or at least alleviate the above described problems, the inventors have found the following solution:

According to one aspect there is provided:
a moisture sensor for measuring moisture in a building, comprising:
  a flexible carrier for attaching said sensor to a floor or inner wall of a building;
  a resonant circuit printed on said carrier;
  a first antenna printed on said carrier, arranged to receive an electromagnetic signal within a first frequency range of 9 kHz to 11 MHz, to convert said signal into an AC voltage, which voltage is arranged to alternate within said first frequency range; and to feed said voltage to said resonant circuit, wherein said first antenna is further arranged to emit an electromagnetic signal indicative of the impedance of said resonant circuit;
  an encapsulation layer sealing said moisture sensor, which layer comprises a humidity permeable portion;
wherein said resonant circuit comprises a moisture reactive element comprising:
  a first and a second inert electrode comprising electrochemically substantially inert material, each electrode being arranged as a layer and
  a hygroscopic solid or solidified electrolyte arranged as a layer and spatially between said inert electrodes, which hygroscopic solid electrolyte at least in the presence of moisture forms mobile ions selected from a group consisting of cations and anions, and which hygroscopic solid electrolyte provides a varying complex impedance at least in response to said alternating voltage being applied across said inert electrodes.

Alternatively or additionally to what is stated above, the moisture reactive element comprises:
  a first and a second inert electrode comprising electrochemically substantially inert material,
  a hygroscopic solid electrolyte arranged as a layer and spatially between said inert electrodes, which hygroscopic solid electrolyte at least in the presence of moisture forms ions, which ions are mobile in response to an alternating electric field, having a frequency between 9 kHz and 11 MHz, applied across said electrolyte, and which hygroscopic solid electrolyte provides a complex impedance at least in response to said alternating electric field, which complex impedance varies with a varying water content of said electrolyte.

In other words said hygroscopic electrolyte is preferably arranged such that it at least in the presence of moisture forms mobile ions selected from a group consisting of cations and anions. In more detail, the ions are mobile when an alternating electric field within said first frequency range is applied across said electrolyte. Hence, the moisture reactive element provides a complex impedance at least in response to said alternating voltage, which complex impedance varies with the moisture content of the electrolyte.

Further, the electrolyte is preferably arranged such that the mobility of at least one group of ions varies with a varying moisture content or water content of the electrolyte. According to one example the mobility of the at least one group of ions is increased with an increased moisture or water content of the electrolyte.

In general, humidity sensors are divided into relative humidity (RH) sensors and absolute humidity sensors depending on their difference in measurement units. Further, the ones that are based on electrical impedance changes are commonly divided into two different types, resistive- and capacitive-type sensors. The resistive-type sensors are based on a change of the real part of the impedance of the sensing material with a change in the surrounding humidity while the capacitive-type sensors are based on a change of the imaginary part of the impedance. The most common capacitive-type humidity sensors uses a dielectric material as the active sensing material included in an interdigitated electrode configuration. Absorption of water into the dielectric layer changes its permittivity, thus modulating the capacitance.

In relation to this invention a complex impedance is an impedance with an imaginary part that is not equal to 0.

According to a second aspect there is provided:
a system comprising
  a moisture sensor arranged as described above, and
  a reader comprising:
    means (signal generator) for generating and emitting an electromagnetic signal sweeping from a first to a second frequency within said first frequency range;

a circuit arranged to receive a electromagnetic signal from said sensor;

means arranged to convert said received electromagnetic signal to a value indicative of the presence of moisture in said sensor.

According to a third aspect there is provided:

a system comprising a first moisture sensor arranged as described above, a second moisture sensor arranged as described above having a predetermined electrolyte moisture level and being sealed with an moisture impervious seal to maintain the said predetermined electrolyte moisture level, and a reader comprising:

means for generating and emitting an electromagnetic signal having a first predetermined frequency;

an electric circuit comprising:

antenna means arranged to receive a first reflected impedance from said first sensor and a second reflected impedance said second sensor, respectively;

comparison means arranged to compare said first impedance to second impedance and to determine the moisture level of said first sensor based on the result of the comparison of said first and second moisture levels.

According to a fourth aspect thereof, the invention relates to use of a moisture reactive element as described above in a resonance circuit for determination of the presence of moisture, or the amount of moisture in the vicinity of the moisture reactive element.

The invention is advantageous in that it provides a wirelessly readably sensor that is easy to manufacture by means of printing techniques and/or in a roll-to-roll process. In other words, because of its simplicity, the moisture sensor could be manufactured by printing techniques and integrated into a low-cost passive electronic sensor label. Further, the electrolyte is preferably printable, such that it may easily be arranged on the carrier.

The sensor is advantageous as it may e.g. be applied to an intermediate layer of a building structure, as a step in the process of completing this surface. According to one example the sensor is applied within a putty, concrete or a similar material that has been applied to the building structure, while the putty etc. is still soft. A wireless reading of the sensor may thereafter be used to determine when the material has cured sufficiently, such that the craftsmen may continue with the next step in the completion of the building wall, floor or ceiling.

When the building surface has been completed the sensor may additionally or alternatively be used to monitor the moisture level at the sensor at regular intervals. In this way an increased moisture level may be readily observed and taken care of at an early stage.

According to the working principle of the moisture sensor the resonance frequency of the resonance circuit is indicative of the amount of or presence of moisture in the electrolyte, as the complex impedance of the moisture element varies with the moisture content of the electrolyte therein. This variation is mainly due to that in response to an increased amount of moisture in the electrolyte, the movability of at least one ion group in the electrolyte is increased, and to some extent also due to that the number of ions formed in the hygroscopic electrolyte is increased. The presence of moveable ions in the electrolyte facilitates a polarization of the electrolyte by means of an applied electric field between the inert electrodes, i.e. an electric field applied across the electrolyte of the moisture reactive element, as the applied electric field will cause a redistribution of the ions. In more detail, cations are attracted towards the negative electrode, and anions towards the positive electrode and at least some of the ions are movable within the electrolyte. A periodical switch of the polarity of the applied electric field makes the ions move to and from between the pair of electrodes, provided that the frequency is sufficiently low. If the frequency instead is too high, there will not be sufficient time for the ions to move any substantial distance before the field is switched again, as a result the ions stay in substantially the same place in the electrolyte, and no varying polarization of the electrolyte is achieved. This may also be expressed as the polarization of the electrolyte being slow. In more detail, for said too high frequencies, the electrolyte mainly displays a change in dielectric constant related to the change in humidity content, and no substantial change in the polarization capability. On the other hand, although the ions may not be sufficiently mobile to move all the way from one electrode to the other, before the direction of the electric field is switched, a smaller displacement of the ions also polarizes the electrolyte, and may be sufficient to establish an easily detectable polarization of the electrolyte.

In relation to this invention, when reference is made an ion or group of ions of the electrolyte being mobile, it means that the ion or group of ions is mobile at the frequency of the electromagnetic radiation which the antenna is arranged to receive, and at the frequency of the alternating field applied across the electrolyte, and across the inert electrodes of the moisture reactive element.

According to one example, the first antenna is arranged to receive an electromagnetic (EM) signal within a frequency range from 9 kHz up to 11 MHz, or up to about 8.8 MHz, or up to about 7 MHz, or up to about 3.5 MHz, or up to about 2.5 MHz, or up to about 1 MHz.

In further examples the first antenna is arranged to receive an EM-signal within a frequency range of 25 kHz to 8800 kHz, or 50 kHz to 2000 kHz, or 10 kHz to 3500 kHz According to further examples the first antenna is arranged to receive an EM-signal within a frequency range of 25 kHz to 500 kHz, or 50 kHz to 200 kHz, or 10 kHz to 150 kHz or 400 kHz-700 kHz or 800 kHz to 1 MHz.

According to further exemplifying embodiments of the moisture sensor, it is configured to operate in any one of, or combinations of, the following frequency bands:

9-30 kHz:

30-60 kHz:

60-120 kHz:

120-148.5 kHz:

315-600 kHz:

400-600 kHz:

3155-3400 kHz:

6765-6795 kHz:

7400-8800 kHz:

10.2-11.0 MHz:

According to one example, when a direct current (dc) voltage is applied across the electrolyte of the moisture reactive element, electric double-layers are usually built up at the electrolyte/electrode interfaces. Mobile cations and anions in the electrolyte layer migrate towards the negatively charged and the positively charged metal electrode, respectively, while the immobile anions and cations remain close to the positively charged and the negatively charged metal electrode, respectively. In the case of an AC voltage applied across the moisture reactive element, the frequency response of the moisture reactive element depends on the frequency of the voltage applied thereto. The area of the interface between the electrolyte and the electrode, in combination with the thickness of the electrolyte determines the properties of the moisture reactive element for a predetermined selection of materials for the electrodes and the electrolyte.

In summary, it is advantageous that the variation of the complex impedance of the moisture reactive element, in response to a variation in the moisture content in the electrolyte, is sufficiently large in order to provide a detectable difference in frequency response related to different moisture levels of the electrolyte at least when the moisture reactive element is incorporated in a resonance circuit.

In essence the invention provides a device that allows for measurement of moisture in building structures without any damage to the surface of the building structure. The moisture sensor includes a flexible carrier carrying an antenna for receiving EM-radiation between 9 kHz and 11 MHz, or between 10 kHz and 1 MHz, and a resonant circuit comprising a moisture reactive element. The moisture reactive element comprises a hygroscopic electrolyte arranged between a first and a second electrode, wherein the electrolyte in the presence of moisture forms mobile ions and provides a complex impedance at least in response to said alternating voltage, which complex impedance varies with the moisture content of the electrolyte.

The invention is built on an insight that by providing a wirelessly readable moisture sensor arranged as described above in an intermediate layer of the building structure, the presence of moisture can be continuously detected by means of e.g. a hand-held reader, which activates the sensor by means of electromagnetic signals. This eliminates the need for introducing a measurement sensor through a drilled hole in the building surface, and facilitates the monitoring of the moisture level in the building surface.

The inventors have realized that the ionic relaxation, which take place in e.g. polyelectrolyte at specific frequency ranges, may be used as a sensing probe in wireless moisture sensors. The various relaxation mechanisms that take place are e.g. dipolar and ionic relaxations as well as double-layer formation when sandwiched between e.g. two metal electrodes.

According to one embodiment, the flexible carrier is provided with an adhesive layer for attaching said moisture sensor to a floor or inner wall of a building. The adhesive layer facilitates easy installment and application of the moisture sensor in different locations, such as to, or in, e.g. internal/external portions of walls or floors of buildings. Adhesive of various types are considered having set, cure, anneal, or fastening times between 0 and 100 seconds, or between 0.01 and 10 seconds, or between 0.5 and 2 second.

The adhesive may be based any adhesive material having suitable properties in relation to the intended application and the surface material it should be used with, or stick onto. The adhesive may for example be based on rubber, acrylic or silicone.

According to one embodiment all of the inert electrode layers and the hygroscopic electrolyte layer are arranged substantially in parallel. According to one embodiment said layers are stacked on top of each other.

According to one embodiment the hygroscopic solid electrolyte is sandwiched between the inert electrodes. In other words, the solid electrolyte is arranged between two electrode layers, which face each other.

According to one embodiment the interface area between the hygroscopic solid electrolyte and an a respective one of said first and second inert electrodes is smaller than the surface area of said respective one of said first and second inert electrodes. In other words, the interface area between the hygroscopic solid electrolyte and said first electrode is smaller than the surface area of said first inert electrode; or the interface area between the hygroscopic solid electrolyte and said first electrode is smaller than the surface area of said second inert electrode.

According to one embodiment the interface area between the hygroscopic solid electrolyte and said first electrode is smaller than the surface area of said electrolyte; and the interface area between the hygroscopic solid electrolyte and said first electrode is smaller than the surface area of said electrolyte.

That the electrolyte extends outside the electrode, or that the interface area between the electrolyte and the electrode is smaller than the surface area of at least one the electrode, is advantageous in that it facilitates moisture ingress into the electrolyte. Further, it is also advantageous in that it aids in preventing accidental short cuts between the electrode and other near by circuitry, such as the other electrode of the moisture reactive element.

According to one embodiment said electrolyte fully covers at least one of said inert electrodes. In other words, the surface area of at least one electrode is smaller than the surface area of the electrolyte, and according to one example the interface between the electrolyte and electrode extends to the surface edge of at least one of the electrodes. According to this example, the interface between the electrolyte and the electrode is in other words fully or partly encircled by portions of the electrode surface devoid of any electrolyte.

According to one embodiment said inert electrodes are in direct electrical contact with said electrolyte. This is advantageous as it prevents an electrochemical reaction between the electrode and the electrolyte.

According to one embodiment at least one of said first and second inert electrodes is provided with apertures or several through-holes having a diameter of 0.1 nm-1 mm or 1 nm-10 μm or 10 nm to 1 μm. This is advantageous at it facilitates moisture ingress into the electrolyte between said electrodes.

According to one embodiment said inert electrodes are in direct electrical contact with said electrolyte. This is advantageous as it normally improves the polarizing effect of an electrical field applied between said first and second electrodes.

According to one embodiment said electrolyte is polarizable within said first frequency range. Hence, the ions in the electrolyte are sufficiently mobile, in response to a predetermined humidity and/or a predetermined voltage generated by said moisture sensor antenna at normal use of the sensor, to provide a redistribution of charges, which redistribution results in a complex impedance of the electrolyte, which impedance varies with the moisture uptake of the electrolyte as explained above.

That the electrolyte is polarisable is beneficial as it provides for the complex impedance of the moisture reactive element, which makes the resonance frequency more pronounced.

According to one embodiment said resonant circuit and said antenna are both arranged on the same side of said carrier.

This is advantageous as it facilitates the manufacturing of the sensor, as all circuit components may be printed on the same side of the carrier.

According to one embodiment said circuit is a passive resonant circuit.

In relation to this invention a passive circuit is a circuit which is not directly connected to a power supply, but which circuit normally extracts the energy from a received electromagnetic signal from the reader.

This is advantageous as it provides a long time of usage, as the moisture sensor is not dependent on the life of an included a battery.

According to one embodiment said electrolyte is a polymeric electrolyte, or polymer-based electrolyte. The use of a polymeric, or polymer-based, electrolyte usually provides low fabrication costs, ease of processing and manufacturing and high sensitivity. Polymer-based electrolytes include e.g. the following classes of solid electrolytes: (i) polymer electrolytes which are composed of a neutral polymer that is a matrix in which a salt is added. (ii) Polyelectrolytes are composed of polymer chain carrying ions.

Polyelectrolytes represent a family of solid-state electrolytes where the ionic charges are carried by the polymer chains while counter ions are condensed around the polymer chains. Polyelectrolytes are hygroscopic materials that can dissociate into ions upon water absorption. Various relaxation mechanisms (dipolar and ionic relaxations as well as double-layer formation when sandwiched between two metal electrodes) take place in the polyelectrolyte at different frequency ranges.

According to one embodiment said electrolyte, at least in the presence of moisture, forms mobile ions selected from a group consisting of cations and anions, as well as immobile ions selected from a group consisting of polycations and polyanions.

According to one embodiment an encapsulation layer or protective layer covers the sensor circuitry and optionally the whole of the moisture sensor surface. Preferably, the protective layer is made of a material which is durable, such as a plastic over-laminate or a printed varnish layer. The printing of a varnish is advantageous as it facilitates the application of the protective layer locally on the sensor. The protective layer or encapsulation layer may also be a layer comprising Teflon® and/or a moisture permeable material such as Gore-Tex®.

The adhesive layer may be provided to the moisture sensor as on outer-most layer, e.g. after the protective layer has been applied.

According to one example said resonant circuit, said antenna and said adhesive layer are all provided on the same side of said carrier, wherein said adhesive according to one example is arranged outside and around said circuitry, such that it does not cover the moisture sensor.

According to another example, said resonant circuit and said antenna are both provided on the opposite side of said carrier compared to said adhesive layer, wherein said adhesive preferably covers more than 60% of the carrier layer.

According to a one aspect of the present invention, it relates to a method of producing a moisture sensor, which method comprises providing a flexible substrate, printing an antenna and a resonance circuitry on said flexible substrate. The method further comprising the steps of providing a first electrode layer on said substrate, printing a layer of hygroscopic electrolyte on said first electrode, and providing a second electrode layer on said hygroscopic electrolyte. Advantageously, the moisture sensors may be produced by efficiently using conventional techniques at low costs. Furthermore, according to an embodiment, the first and second electrodes are provided by means of printing.

According to one embodiment, the method of producing comprising the step of providing a lacquer layer. The lacquer layer advantageously provide insulation and/or protection for the first and second electrodes, and the electrolyte, wherein the lacquer layer may be arranged in a sandwiched, or interposed, configuration. The lacquer layer may further be patterned, or interrupted and used for defining the contact areas between the first and second electrodes and electrolyte. Also, the lacquer layer may be used and patterned for defining an active region of the moisture reactive element formed by said electrolyte and first and second electrodes. The active region may be open and exposed to ambient, or surrounding, humidity conditions.

According to a further aspect of the present invention, it relates to the use of the moisture sensor having a resonance circuit comprising a moisture reactive element. The moisture sensor may for example be used in various devices or products for moisture measuring purposes, wherein wireless measurement of the moisture level is suitable. For example, moisture measurement of the functionality and tightness of the packaging of goods or food products.

DEFINITIONS

In relation to this invention the term "flexible" means that something is capable of being bent or rolled normally by the application of a minor to medium hand force.

In relation to this invention the term "building structure" refers to an externally or internally arranged portion of the floor, ceiling or wall of a building, e.g. a bathroom wall.

In relation to this invention the term "antenna" refers to a structure that is capable of receiving an electromagnetic field and to convert this into a voltage or current. In the case of magnetic coupling between two inductors or two coils, each inductor or coil may represent one antenna.

According to one embodiment the antenna is arranged as a loop antenna. According to another embodiment the antenna is arranged as a half-wave dipole antenna. Advantageously, this corresponds to designs which are straight-forward to manufacture. According to yet one embodiment, the antenna is arranged as a half-wave folded dipole antenna. This is advantageous as it facilitates the arrangement of the antenna in a more confined way. A dipole antenna can be folded in many different ways, as is known in the art. The antenna may for example be folded with straight angles, e.g. in a meander shape. According to one example the antenna is given a meander shape or the shape of a square wave, having either a constant or varying amplitude. Optionally, one or several of the antenna folds may be obtuse, acute or rounded.

In relation to this invention the term "resonant circuit" refers to a circuit comprising at least an inductor and a capacitor or two component combining these properties, wherein resonance occurs at a particular frequency when the total inductive reactance and the total capacitive reactance are of equal magnitude. The frequency at which this equality holds for the particular circuit is called the resonant frequency. The circuit may be arranged as a series resonant or parallell resonant. The resonant circuit may include a combination of several inductors, several capacitors and/or several resonators as is known in the art.

Normally, the voltage or current in the resonant circuit alternate with substantially the same frequency as the frequency of the received electromagnetic signal.

The electromagnetic signal may be a magnetic coupling between an inductor arranged in the reader and an inductor arranged in the sensor, or it may be a radio signal emitted by the reader, which is received by the antenna of the sensor device.

In relation to this invention "an electrochemically substantially inert material" is a material which does not readily react electrochemically with the hygroscopic electrolyte. Examples of such materials are gold, platinum, palladium, a conducting form of carbon, metal nano particles, and liquid metal alloys such as GaInSn, mercury.

According to one example the top inert electrode is provided by printing a substantially dry paste comprising at least one of said electrochemically substantially inert materials on the electrolyte layer. When a liquid emulsion, dispersion or solution comprising at least one of said electrochemically substantially inert materials is provided as top electrode, the solvent molecules tend to penetrate more into the electrolyte layer, compared to when a dry paste is used. In other words, using a dry a paste as top electrode has the advantage of leaving some of the electrolyte layer intact, such that it may still act as an electronic insulator in the moisture reactive element, as the molecules of the dry paste does not penetrate as far into the electrolyte layer as the molecules of the other materials. Further dry paste may be used for both moisture reactive element electrodes.

According to one embodiment at least one of the inert electrodes comprises carbon, which may be provided in the form a dry carbon paste. The use of carbon is advantageous as it usually provides a more linear frequency response of the circuit related to humidity content in a larger portion of the humidity range.

Do note that there is usually a minor electrochemical reaction between any combination of different materials, but there are some materials that are specifically prone to electrochemical reactions in combination with the electrolyte, e.g. PEDOT:PSS. Such material are obviously not to be regarded as electrochemical inert materials. In more detail, an electrochemical inert material is a material which does not undergo a substantial electrochemical reaction with the electrolyte at the potentials generated across the electrolyte by the signal received from the reader.

In relation to this invention the term "printable electrolyte" refers to any electrolyte having reological properties which makes it suitable for printing e.g. by ink-jet printing or by a roll-to-roll process. Regarding reological properties, electrolyte viscosity may be considered. Exemplifying intervals of electrolyte viscosity (mPas) for different printing methods are:

Inkjet printing: 1-20
   Flexo printing: 20-400
   Screen printing: 1000-100000
   Offset printing: 1000-1.00000
   Gravure printing: 20-200

In relation to this invention the term "hygroscopic electrolyte" refers to any electrolyte (polymer-based, polymeric or inorganic) that posses a water uptake larger than 10% at room temperature, Water uptake is defined as $(W_{wet}-W_{dry})/W_{dry}$, where $W_{wet}$ and $W_{dry}$ are the weights of fully hydrated and dehydrated layer, respectively.

According to one example the composition of the electrolyte is chosen such that the ions can move even without any presence of water, i.e. the ions are not too large and the polymer matrix is permeable for those ions. Due to the electrolyte being hygroscopic the movability of the ions will increase with an increased moisture content.

Electrolyte: According to one embodiment of the invention said electrolyte or electrolyte layer preferably is an organic, organometallic or inorganic material which dissociates partially in ions. The ion conductivity is preferably at least larger than $10^{-7}$ S/cm at 10% RH. The organic electrolyte is preferably a molecular, macromolecular, oligomeric, polymeric electrolyte, selected from a group comprising for example ionic surfactants or ionic detergents, ionic liquids, ionic gels i.e. ionic liquid and a polymer, fatty acids, amino-acid based molecules and polymers (such as proteins), saccharides or polysaccharides, biomolecules and macromolecules with phosphate groups (e.g. DNA, phosphoglycerides, phospholipids), oligoions or polyions.

According to one embodiment of the invention said electrolyte layer comprises an acid-functional homopolymer or homooligomer or an acid-functional copolymer or cooligomer. In other words, the electrolyte layer of said sensor preferably is an oligomeric or polymeric acid having at least one acid-functional group.

Hence, said electrolyte layer preferably comprises additives, which facilitates the operation and/or manufacturing of said sensor device or improve its resistance. For example, said oligomeric or polymeric acid of said electrolyte is preferably cross-linked, in order to reduce its solubility with water, such that e.g. water droplets which condensate on the moisture reactive element do not interfere with the frequency response of the sensor, e.g. by from dissolving the electrolyte film. Further, said oligomeric or polymeric acid is preferably cross-linked by an external cross-linker. It is even more preferred that said external cross-linker has two or more glycidyl groups. Advantageously, said external cross-linker is polyethylene glycol diglycidyl ether (PEG-DEG).

When the electrolyte comprises PSS, silane derivatives, for instance the gamma-glycidoxypropyltrimethoxysilane (A 187 Silquest), may advantageously be used as a cross-linker. The cross-linker may be induced by low temperature annealing treatment (e.g. T<100° C.). The use of this type of cross-linker also facilitates the manufacturing of the moisture reactive element, as the cross-linked electrolyte is less sensitive to that water drops or drops of solvent get in contact with the electrolyte during the manufacturing of the sensor.

According to one embodiment of the invention said oligomeric or polymeric acid of said electrolyte layer is an oligomer or polymer of monomer units having phosphonic acid, sulphonic acid, carboxylic acid or phosphoric acid groups. Said monomer units advantageously have sulphonic acid groups, and even more preferred, said monomer units are styrene-4-sulphonic acid or a salt thereof, such as PSSNa poly(sodium 4-styrenesulfo-nate)

For the purposes of the invention, "a solid electrolyte" or "a solidified electrolyte" means an electrolyte, which at the temperatures at which it is used is sufficiently rigid that particles/flakes in the bulk therein are substantially immobilised by the high viscosity/rigidity of the electrolyte and that it does not flow or leak. In the preferred case, such an electrolyte has the proper rheological properties to allow for the ready application of this material on a support or substrate in an integral sheet or in a pattern, for example by conventional printing methods. After deposition, the electrolyte formulation should solidify upon evaporation of solvent or because of a chemical cross-linking reaction, brought about by additional chemical reagents or by physical effect, such as irradiation by ultraviolet, infrared or microwave radiation, cooling or any other such. The solidified electrolyte preferably comprises an aqueous or organic solvent-containing gel, such as gelatine or a polymeric gel. However, solid polymeric electrolytes are also contemplated and fall within the scope of the present invention. Furthermore, the definition also encompasses liquid electrolyte solutions soaked into, or in any other way hosted by, an appropriate matrix material, such as a paper, a fabric or a porous polymer.

Electrodes: "electrodes" in devices according to the invention are structures that are composed of an electrically conducting material.

In relation to this invention "direct electrical contact" refers to direct physical contact (common interface) between two phases (for example an electrode and electrolyte) that allows for the exchange of charges through the interface. Charge exchange through the interface can comprise transfer of electrons between electrically conducting phases, transfer of ions between ionically conducting phases, or conversion between electronic current and ionic current by means of electrochemistry at an interface between for example counter element and electrolyte or electrolyte and electrochromic element.

Layer: according to one embodiment, the humidity sensor has a laminate structure and consists of "layers" of different materials. These layers can be continuous or patterned or interrupted, and can be applied to each other (self-supporting device) or to a support (supported device). Furthermore, the term layer is intended to encompass all of the same material in the same plane, regardless whether this material is patterned or interrupted in such a way as to form discontinuous "islands" in the plane. The humidity sensor circuitry preferably has a planar configuration.

Direct electrical contact: Direct physical contact (common interface) between two phases (for example counter element and electrolyte) that allows for the exchange of charges through the interface. Charge exchange through the interface can comprise transfer of electrons between electrically conducting phases, transfer of ions between ionically conducting phases, or conversion between electronic current and ionic current by means of electrochemistry at an interface between for example counter element and electrolyte or electrolyte and electrochromic element, or by occurrence of capacitive currents due to the charging of the Helmholtz layer at such an interface.

Further objectives of, features of, and advantages of the present invention will become apparent when studying the following detailed disclosure, the drawing and the appended claims. Those skilled in the art realize that different features of the present invention can be combined to create embodiments other than those described herein.

BRIEF DESCRIPTION OF DRAWINGS

FIGS. 14a and 14b schematically illustrate an embodiment of an integrated moisture sensor, and exemplified manufacturing thereof.

FIG. 15 is a diagram representative of exemplifying result for an integrated moiser sensor.

DETAILED DESCRIPTION OF THE DRAWINGS

Figure 1A:
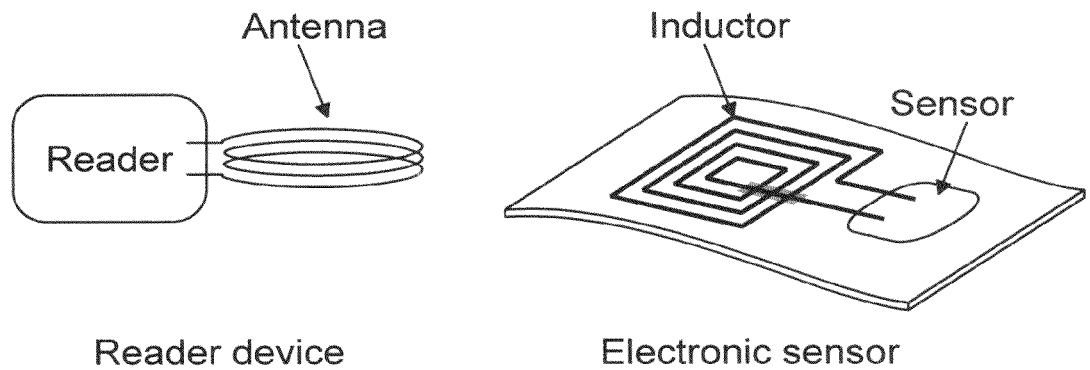
FIG. 1a is a schematic illustration of an inductively coupled sensor system for wireless humidity sensing.

FIG. 1a is a schematic illustration of an inductively coupled sensor system for wireless humidity sensing. The sensor system comprises a reader device and an electronic sensor. The electronic sensor comprises a flexible carrier comprising e.g. paper or plastic, whereon a resonant sensor circuit is arranged. The sensor circuit comprises a moisture reactive element, is connected to an inductor, and is powered remotely via an alternating magnetic field sent from an antenna of the reader. The impedance of the electronic sensor is reflected to the reader device, enabling the humidity sensitive resonance frequency of the electronic sensor to be readout at the reader side. Thus, the humidity level surrounding the electronic sensor and more particularly the moisture reactive element can be read out wirelessly without the need of a power source such as a battery being arranged on the electronic sensor.

Figure 1B:
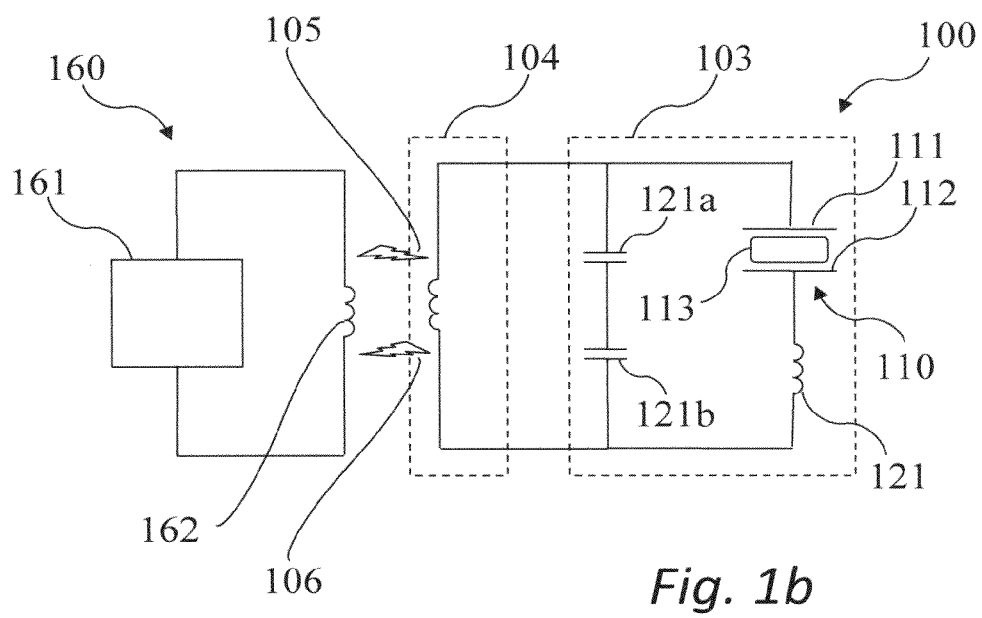
FIG. 1b schematically shows a configuration of a sensor circuit and a reader according to one embodiment of the invention, FIG. 1c schematically shows a crossection of the moisture sensor described in relation to FIG. 1b.
Figure 1C:
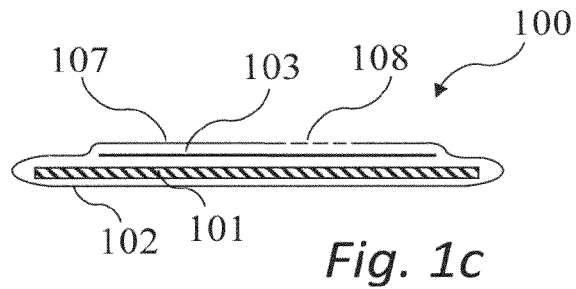

FIG. 1b schematically shows a configuration of a moisture sensor 100 and a reader 160 according to one embodiment of the invention, and FIG. 1c schematically shows a crossection of the moisture sensor described in relation to FIG. 1b.

The circuitry 103, 104 of the moisture sensor comprises a first antenna 104 arranged to receive electromagnetic radiation from a reader 160, and to convert this into a voltage and/or current which modifies a moisture reactive element 110, i.e. an element the properites of which is altered in response to an alteration of the moisture level in the absolute vicinity of the moisture reactive element, of a passive resonant circuit 103. The antenna 104 is connected in parallell with the resonant circuit 103.

In its most basic configuration the resonant circuit comprises only the moisture reactive element arranged in series or parallell with an inductor. The moisture reactive element may also be arranged in series or parallell with at least one inductor and at least one capacitor.

An example of a basic moisture sensor comprises just the moisture reactive element connected in parallell with an inductor, where the inductor serves both as an antenna, for receiving the electromagnetic radiation, and as an inductor, for providing a varying resonance frequency in combination with the moisture reactive element. In other words, the resonant circuit comprises just the moisture reactive element, which in combination with the antenna provides a resonance frequency which varies with the moisture within the moisture reactive element. In order to optimize the frequency response of the circuit the resonance circuit may be arranged with one or more additional capacitors, inductors or resistors.

According to the example illustrated in FIG. 1 the resonant circuit comprises a moisture reactive element 110 connected in serises with an inductor 121. The moisture reactive element 110 and the inductor 121 are in turn connected in parallell with a first and a second serially connected capacitor 121a, 121b.

For all embodiments of the moisture sensor the properites of the antenna as well as the components in the resonant circuit are tuned or selected such that the resulting AC-voltage applied across the electrolyte results in a desired resolution in the frequency response of the moisture reactive element, i.e.

that the difference in polarization of the electrolyte for different moisture levels results in an easily detecable difference in frequency response.

Further the frequency response of the moisture reactive element is also tunable. By e.g. selecting a larger interface between the electrodes and the electrolyte, a higher impedance of the moisture reactive element is provided. In general it is the combined properties of the antenna and the components of the resonant circuit including the moisture sensitive element that will determine the response of the moisture sensor.

According to one example the moisture sensor 100 may be manufactured by providing a flexible substrate whereon the antenna and the resonant circuit is printed by means of conventional methods, such as ink jet printing or roll to roll printing. The moisture reactive element may be printed on the flexible substrate by first printing one of the electrodes 112, thereafter printing a layer of electrolyte 113, and on top of this printing the other electrode 111. A moisture permeable cover may be applied on top of the moisture selective element 108, and finally an encapsulation layer 107 is sealed such that it covers the whole of, or e.g. at least one side of, said flexible substrate but leaving at least a portion of said moisture permeable cover exposed to moisture surrounding said sensor.

In other words, the moisture sensor comprises a flexible carrier 101 provided with an adhesive layer 102 for attaching said sensor to a floor or inner wall of a building. The adhesive layer may be provided on an optional side of the moisture sensor, as long as it allows the sensor to be applied to a building surface.

The moisture sensor further comprises a resonant circuit 103 printed on said carrier 101, as well as a first antenna 104 which is also printed on said carrier. In more detail, the left hand rectangle indicated by a dashed line encircles the antenna portion 104 of the moisture sensor, while the right hand rectangle indicated by a dashed line encircles the resonant circuit portion 103 of the moisture sensor.

The antenna is arranged to receive an electromagnetic signal 105 within a first frequency range of 9 kHz to 11 MHz usually from a reader; to convert the signal into an AC voltage and/or an AC current, which voltage and/or current is arranged to alternate within said first frequency range; and to feed said voltage and/or current to said resonant circuit 103. The received voltage and/or current is modified by the resonant circuit 103 and, the first antenna 104 is further arranged to emit an electromagnetic signal 106 indicative of the impedance of said resonant circuit 103.

The resonant circuit 103 is provided with a moisture reactive element 110, which comprises a first and a second inert electrode 111, 112 comprising electrochemically substantially inert material, as well as a hygroscopic printable solid electrolyte 113 arranged between said electrodes. The electrolyte is arranged such that it at least in the presence of moisture forms ions selected from a group consisting of cations and anions, and which electrolyte provides a complex impedance in response to said alternating voltage. The electrolyte is further arranged such that the movability of at least one category of ions is increased, in response to an increased amount of moisture in the electrolyte.

According to this example the moisture reactive element 110 containing electrolyte is arranged in series with an inductor 121, and the moisture reactive element 110 and the inductor are arranged in parallel with two additional capacitors 121a, 121b, which do not comprise any polarizable electrolyte.

The moisture sensor further comprises an encapsulation layer 107 sealing and protecting said moisture sensor, which layer comprises a humidity permeable portion 108. One of the purposes of the encapsulation layer is to prevent water droplets to be in direct contact with the electrolyte of the moisture reactive element. Upon such contact, the water may penetrate by means of osmosis between the electrodes and dissolve the electrolyte and thus destroy the sensor. The encapsulation should preferably permit vapor to pass into the electrolyte of the sensor, but prevent liquids from entering.

According to one example the sensor is applied on or inside an intermediate surface (wall, floor or ceiling) of a building, such as behind the damp-proof course of a bathroom wall or floor, on top of which course a layer of tile adhesive and later tiles are provided. If desired, the moisture sensor may also be provided e.g. between the damp-proof course and the top layer of the floor or wall.

At any time the sensor circuit may than be read by providing a moisture sensor reader within a reading range of the sensor. The moisture sensor reader emits an electromagnetic signal which is received by the antenna of the moisture sensor. The emitted signal is usually either a signal comprising a single frequency, or a signal comprising a frequency sweep starting at first frequency followed by an increase or decrease of this signal to a final frequency. The increase or decrease of the signal may be a continuous or discontinuous sweep through the intermediate frequencies, i.e. the frequencies intermediate said first frequency and said final frequency.

The received frequency is modified by the resonance circuitry and a resulting frequency, which is dependent on e.g. the frequency of the signal received from said reader as well as the impedance of said moisture reactive element comprising electrolyte, is emitted from said moisture sensor.

The emitted resulting frequency from said moisture sensor is received by said reader, and the value is converted into the corresponding moisture value which is displayed to the user of the moisture sensor reader, e.g. by means of a look-up table.

In other words, the impedance of the resonance circuitry may alternate which alters the resonance frequency of the resonance circuitry which, in turn, may be detected, or measured, wirelessly using the moisture sensor reader.

For the purpose of reading the moisture sensor, there are a number of suitable readers known in the art of wireless communication. Any reader which can emit suitable signal, with a suitable frequency variation, receive the electromagnetic signal emitted from said moisture sensor, and which can be programmed to convert the received electromagnetic signal to a moisture value may be used.

Figure 2A:
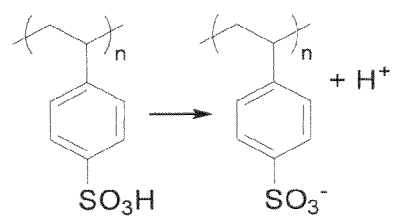
FIG. 2a is a representation of the chemical structure of PSS:H in its protonated and deprotonated form, respectively.
Figure 2B:
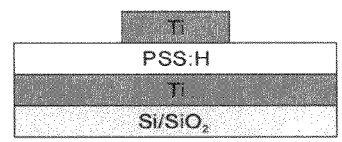
FIG. 2b schematically illustrates one example of the moisture reactive element.

FIG. 2a illustrates the chemical structure of PSS:H in its protonated from (left) and its deprotonated form (right).

Below detailed examples are given, wherein low frequency relaxation phenomena in solid electrolytes is used as the sensing mechanism in a wireless humidity sensor system or a moisture sensor system. In more detail, the RH dependence on the real and the imaginary parts of the total impedance of an 80 nm thick solid-state polyanionic polyelectrolyte named poly(styrenesulfonic acid) or PSS:H, sandwiched between two titanium electrodes forming a vertical capacitor structure or an impedance type structure, was analyzed with impedance spectroscopy at different levels of the relatice humidity RH (10% to 90% RH). The polyelectrolyte moisture reactive element, corresponding to the humidity sensitive part, was then connected to an additional capacitor and inductor to form a resonance circuit from which the humidity level was readout wirelessly by monitoring the resonance frequency.

Example 1

The moisture reactive elements were manufactured by spin-coating a thin film (80 nm) of PSS:H onto a global titanium electrode previously vacuum deposited onto a silicon wafer. The PSS:H solution (provided by AGFA-Geveart) was further diluted with deionized water and then filtered using a glass microfiber filter (GMF) membrane whose pore's diameter was about 1 µm. After deposition, the polymer film was annealed under vacuum at 110° C. for 90 s. On top of the polymer film circular titanium electrodes were vacuum deposited through a shadow mask. The resulting cylindrical capacitors or moisture reactive element had a capacitor plate area or an electrode area of approximately $7 \times 10^{-4}$ cm$^2$.

The polyelectrolyte moisture reactive elements were characterized by impedance spectroscopy with a high resolution dielectric analyzer (Novocontrol Technologies GmbH). The amplitude of the AC voltage was 0.1 V and the frequency was swept or scanned from 1 MHz to 100 Hz. Each measurement was conducted at different levels of the RH using a Challenge 160 environmental chamber (Angelantoni Industries). The temperature was held constant at 20° C. while the RH was varied from 10% to 90% RH in steps of 10% RH. The moisture reactive elements responded rapidly to changes in the RH (~1 min), but to ensure that the absorbed water was equilibrated with the vapor phase, the impedance measurement at each RH level was recorded 30 min after the RH was set to a specific level. The impedance characteristics of the polyelectrolyte moisture reactive elements were recorded on the form $Z=Z_{Re}(f) jZ_{Im}(f)$, where $Z_{Re}$ and $Z_{Im}$ represent the frequency (f) dependent real and imaginary parts of the total impedance Z.

Figure 3:
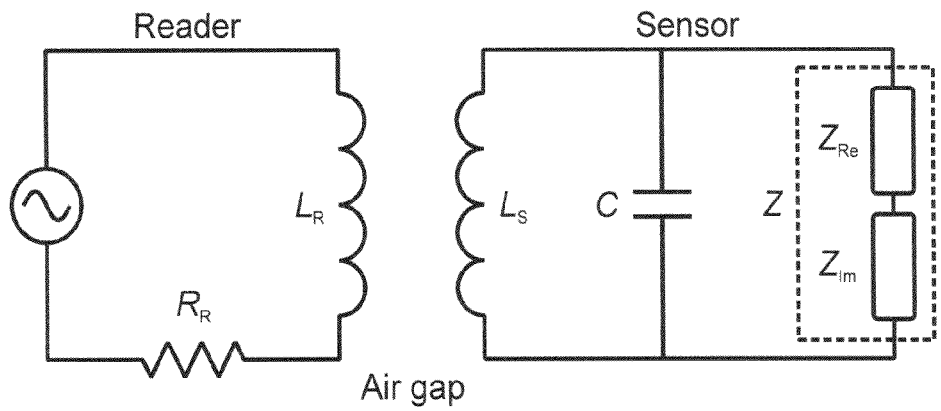
FIG. 3 schematically illustrates a circuit configuration of one example of a moisture sensor and a moisture sensor reader.

One example of the circuitry of the moisture sensor and the reader or reader device is illustrated in FIG. 3. According to this specific example, a reader device, having a setup comprising a resistor $R_R=1 \Omega$ and an inductor $L_R=35$ µH connected in series with a signal generator is provided. The reader was separated from the moisture sensor via an air gap of 1 cm. In the sensor circuit, with $L_S=8$ µH and C=6.6 nF, the impedance element Z ($Z=Z_{Re}+jZ_{Im}$) corresponds to the polyelectrolyte-based moisture reactive element, an 80 nm thin layer of PSS:H sandwiched between two titanium electrodes. The sensor is powered by the reader via inductive coupling. The impedance of the sensor is then reflected to the reader resulting in that the resonance frequency of the sensor, which corresponds to the measured humidity level, can be analyzed at the reader.

The wireless readout was achieved using a reader antenna connected to an E4407B spectrum analyzer (Hewlett Packard). The output signal (2 mW) of the spectrum analyzer was sourcing the reader antenna, which was physically separated from the sensor circuit with an air gap of 1 cm. The reader antenna consisted of an antenna coil ($L_R$) connected in series with a resistor ($R_R=1 \Omega$); while the moisture sensor circuit was composed of a coil ($L_S$), a capacitor (C) and the polyelectrolyte moisture reactive element connected in parallel. Since the impedance of the secondary side circuit (the sensor circuit) will be reflected to the primary side (the reader); the resonance frequency of the sensor circuit can be wirelessly readout utilizing the reader antenna. This was done by analyzing the frequency response of the reader antenna using the spectrum analyzer. The reader and sensor coils were fabricated by hand and their inductance values were estimated experimentally to be $L_R=35$ µH and $L_S=8$ µH. The value of the additional capacitor in the sensor circuit was C=6.6 nF. The measurements performed on the sensor circuit involved the same equipment and followed the same procedure as described for the measurements performed on the polyelectrolyte capacitors to control the RH. To ensure that the observed shift of the resonance frequency originated only from the polyelectrolyte capacitor, the other circuitry of the sensor circuit was placed outside the climate chamber.

When a dc voltage is applied to the polyelectrolyte moisture reactive element, electric double-layers are built up at the polyelectrolyte/metal electrode interfaces. Mobile protons ($H^+$) in the polyelectrolyte layer migrate towards the negatively charged metal electrode while the immobile polyanions ($PSS^-$) remain close to the positively charged metal electrode. In the case of an ac voltage applied across the polyelectrolyte moisture reactive element, the response or polarization characteristics of the moisture reactive element depend on the frequency of the voltage. In the frequency range of this study, two different relaxation phenomena can be identified by analyzing the real and the imaginary parts of the impedance.

Figure 4A:
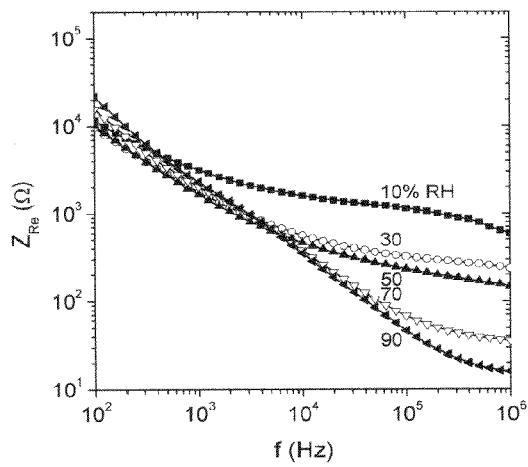
FIGS. 4a and 4b are diagrams illustrating the real and imaginary part of the impedance of a moisture reactive element as a function of frequency for different levels of RH.
Figure 4B:
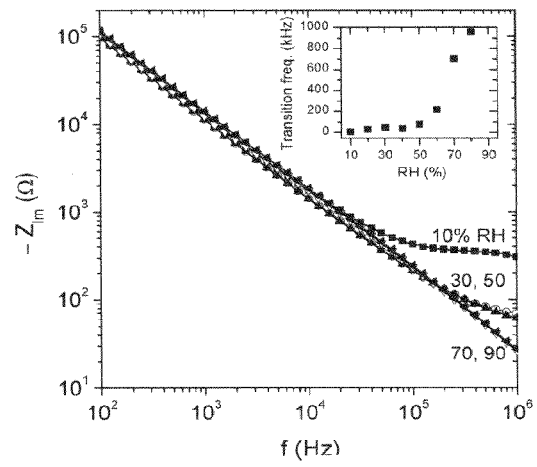

The real part $Z_{Re}$ and the imaginary part $Z_{Im}$ of the impedance of the polyelectrolyte-based moisture reactive element, i.e. a 80 nm thin PSS:H layer sandwiched between two titanium electrodes) are given as functions of frequency for different RH levels (presented in steps of 20% RH between 10% to 90% RH for clarification), in FIGS. 4a and 4b, respectively. The insert in FIG. 4b shows the evolution of the transition frequency, representing the frequency where $|Z_{Im}|=|Z_{Re}|$, versus the RH. Both $Z_{Re}$ and $Z_{Im}$ are functions of the frequency and the RH. $Z_{Re}$ starts to show RH dependence at frequencies above about 800 Hz, while $Z_{Im}$ starts to show RH dependence at considerably higher frequencies (about 60 kHz). Note that $Z_{Im}$ at 30% and 50% RH and at 70% and 90% RH, respectively, are harder to distinguish from each other. At 10% RH, $|Z_{Im}|=|Z_{Re}|$ at ~12 kHz. This frequency, here called the transition frequency, represents the transition between the two relaxation mechanisms. Below the transition frequency, $|Z_{Im}|>|Z_{Re}|$; thus indicating a dominant capacitive character of the impedance. The high value of the imaginary impedance found in this low frequency region, which corresponds to a large effective capacitance ($C_{Eff}$~20 µF cm$^{-2}$ at 100 Hz, $C_{Eff}=[2\pi f |Z_{Im}|]^{-1}$), is associated with the formation of electric double-layers at the polyelectrolyte/metal electrode interfaces. Above the transition frequency, $|Z_{Re}|>|Z_{Im}|$, i.e. the impedance acquires a dominant resistive character. This is believed to originate from dissociated protons migrating away from the polymer chains in the oscillating electric field. This is referred to as ionic relaxation. The transition between these two relaxation mechanisms is suddenly shifted to significantly higher frequencies above 50% RH, see inset in FIG. 4b). Above 100 kHz, $|Z_{Re}|>|Z_{Im}|$ between 10% and 50% RH while $|Z_{Im}|>|Z_{Re}|$ at higher RH levels, which means that, the resistive part of the impedance dominates in dry conditions; while the capacitive dominates in humid conditions. Hence, the moisture reactive element is neither classified as a capacitive-type sensor nor as a resistive-type sensor, but rather as a hybrid of both types: here referred to as an impedance-type sensor.

To complete the moisture sensor and obtain a humidity sensitive resonance circuit, an inductor ($L_S$) was added in parallel to the polyelectrolyte moisture selective element, as is illustrated in FIG. 3. An inductor in the form of a circular loop antenna with $L_S=8$ µH was used in our study. Planar inductors with such inductance value can be manufactured using low-cost and high volume manufacturing techniques today. Adding a capacitor (C=6.6 nF) in parallel to the polyelectrolyte moisture reactive element and the coil ($L_S$) shifts the resonance frequency range of the sensor circuit to the specific RH sensitive frequency region and creates a more well-defined resonance peak. The addition of the capacitor (C) in parallel to the polyelectrolyte capacitor resulted in a more pronounced capacitive behavior of the impedance characteristics of these two capacitive elements alone. The imaginary part of this impedance was higher than the real part independently of the frequency and the RH. The imaginary part showed a weak RH dependence above 20 kHz while the real part showed a clear RH dependence above 4 kHz. The electrical circuit of the resulting sensor circuit is shown in FIG. 3 together with the circuit of the reader setup. As a consequence of the inductive coupling between the two coils the impedance of the sensor circuit will be reflected to the reader circuit, resulting in that the resonance frequency of the sensor circuit can be wirelessly readout at the reader side.

Figure 5:
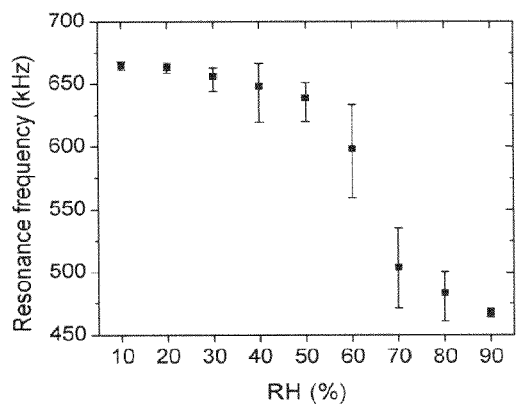
FIG. 5 is a diagram of the resonance frequency of a moisture sensor versus the RH, when read wirelessly. The symbols represent the average of three sensors and the error bars represent min and max values.

The configuration of the sensor circuit results in that a change in $Z_{Re}$ and $Z_{Im}$, of the polyelectrolyte moisture reactive element, influences the resonance frequency. The resonance frequency of the resulting sensor circuit is RH dependent giving the highest resonance frequency for the driest conditions, see FIG. 5. The resonance frequency is about 665 kHz at 10% RH and decreases in a non-linear fashion down to 468 kHz at 90% RH. Three different regimes of the resonance frequency are observed: (i) between 10% and 50% RH the resonance frequency decreases slightly (from 665 kHz to 639 kHz, corresponding to a sensitivity (S) of 0.65 kHz/% RH assuming a linear dependence in this regime), (ii) between 50% and 70% RH the resonance frequency drops drastically (from 639 kHz to 504 kHz) and defines the most sensitive region for the sensor with S=6.75 kHz/% RH; and (iii) above 70% RH the resonance frequency continues to decrease (from 504 kHz to 468 kHz at 90% RH) with S=1.80 kHz/% RH. Hence, the sensitivity of the sensor is not constant versus the RH. This can be explained from previous observations and models for proton transport in solid electrolytes. In a dry film protons are localized by electrostatic interaction in proximity to the sulfonate groups of the polyanions. Upon absorption of water, hydronium ions ($H_3O^+$) are formed that screen this electrostatic interaction. This results in lower activation energy for proton transport. The conductivity mechanism at relatively low concentrations of hydronium is likely taking place as "vehicular" transport, in which proton migration is assisted by translational dynamics of larger species, "vehicles", here identified as $H_3O^+$. This mechanism of proton transport is likely the origin of the moderate increase of the transition frequency in the 10% to 50% RH region (FIG. 4b) as well as the first plateau, in the same RH range, of the resonance frequency of the sensor circuit (FIG. 5). Between 50% and 70% RH, a drastic change of the transition frequency and the resonance frequency are observed. At those hydration levels, the amount of absorbed water is large enough to provide percolation paths, in which proton transport takes place via hopping between absorbed water molecules. This mechanism is frequently termed as the Grotthuss mechanism or structure diffusion. At higher humidity levels, the transition frequency is expected to saturate since the proton mobility is known to reach a maximum at high humidity levels.

In other words, a thin polyelectrolyte proton membrane sandwiched between two electrodes may constitute the sensor device for wireless humidity sensing. The microscopic mechanisms that are responsible for the humidity sensing discussed in relation to this experiment is believed to be due to the proton motion within the membrane, either migration away from the polymer chains (resistive character) or accumulation along the metal surface within electric double-layers (capacitive character). Those two events overlap such that both the real and the imaginary parts of the impedance vary with the relative humidity. As a consequence, when a polyelectrolyte is used as the "dielectric medium" in a moisture reactive element, the device is neither a pure resistive-type sensor nor a pure capacitive-type sensor. The achievement of wireless sensing by connecting an inductor to moisture selective sensor via an additional component provides direct translation of the humidity dependent proton motion into a shift in the resonance frequency of the sensor circuit used. The impedance-type sensor circuit is a simple device that can be integrated into a low-cost passive electronic sensor label that can be manufactured using common printing technologies of today.

Example 2

Figure 6:
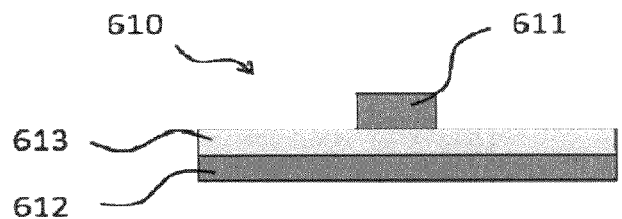
FIG. 6 schematically illustrates the cross-section of an embodiment of the moisture reactive element.
Figure 7:
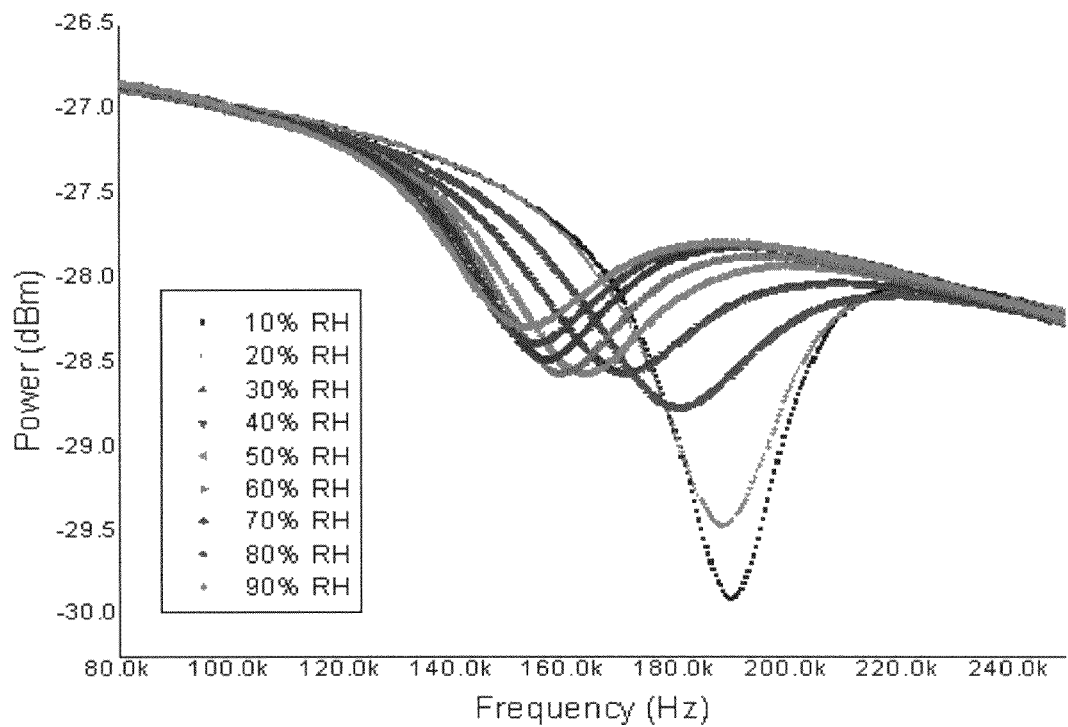
FIG. 7 is a diagram representative of wireless readout output from an embodiment of the moisture sensor.
Figure 8:
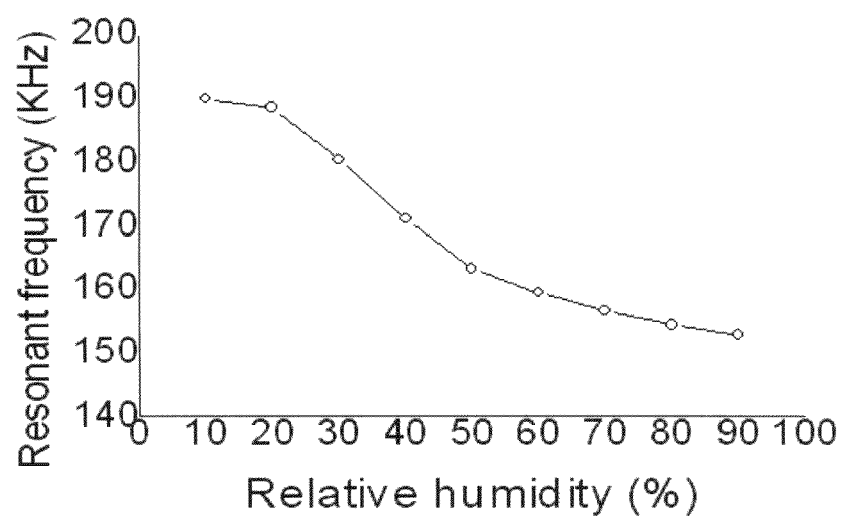
FIG. 8 is a diagram representative of the evolution of the resonant frequency versus relative humidity associated with an embodiment of the moisture sensor.
Figure 9:
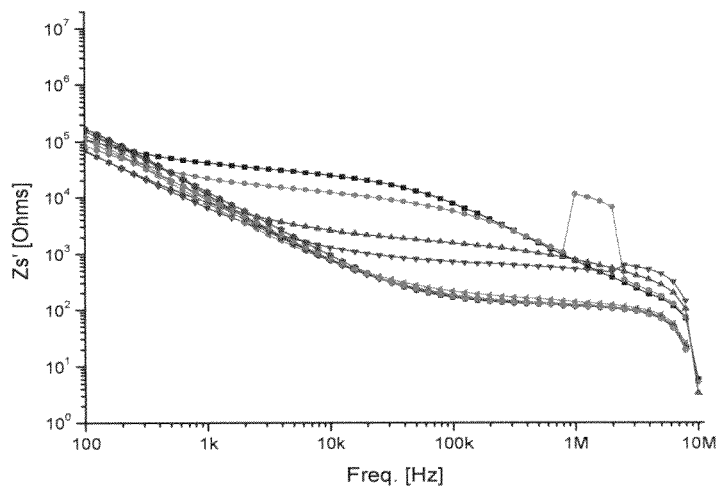
FIGS. 9, 10, 11 and 12 are diagrams representative of the real part, imaginare part, and the phase shift of the impedance, and the capacitance of the a moisture active element as a function of frequency for different levels.

With reference to FIG. 6, an exemplifying embodiment of a moisture sensor 610 is shown. The moisture sensor comprises and may be fabricated from materials that can be printed, or laminated, wherein the bottom electrode 612 may be formed by patterning an Al foil (9 µm-thick) on plastic films. The electrolyte comprises a polystyrene sulfonic acid) sodium salt (PSSNa) (M.W 500,000) and is screen printed on the Al foil to form a 5-10 µm-thick layer. A circular top carbon electrode is afterwards screen printed on top of PSSNa, giving rise to the "dot-type" architecture for the sensor. The wireless readout output from the spectrum analyzer are displayed in FIG. 7, while the evolution of the resonant frequency versus humidity is summarized in FIG. 8. The evolution of resonant frequency versus relative humidity is clearly shown. A shift of resonant frequency from 190 kHz to 150 kHz is observed when relative humidity increases from 10% to 90%.

In FIGS. 9-12, frequency dependent operational and functional properties of the moisture active element, e.g. based on the 'dot'-type structure, are presented. As illustrated, in frequency region up to ~10 MHz, the sensor shows change of its impedance versus humidity. Hence, the moisture sensor, based on wireless humidity sensing via ion-motion, may be operational up to, and likely beyond, 10 Mhz, such as up toll MHz region.

Figure 10:
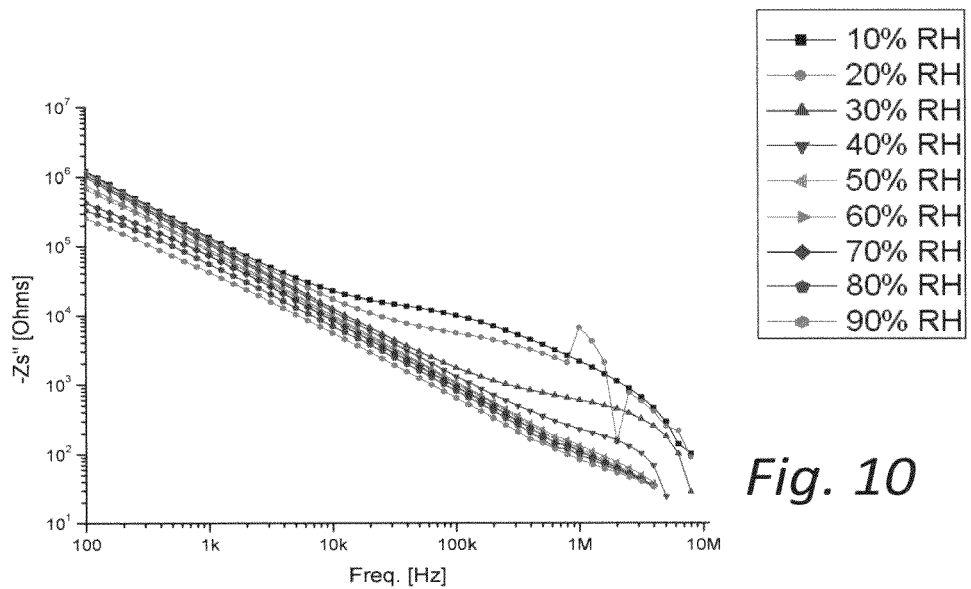
Figure 11:
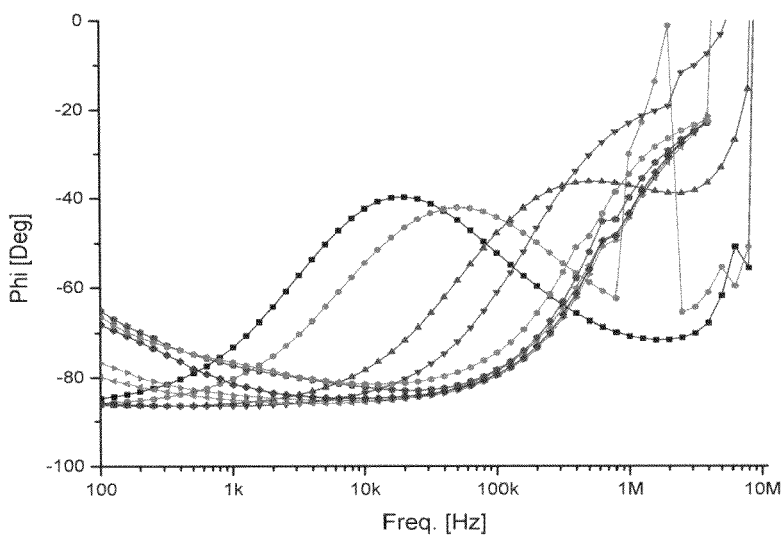
Figure 12:
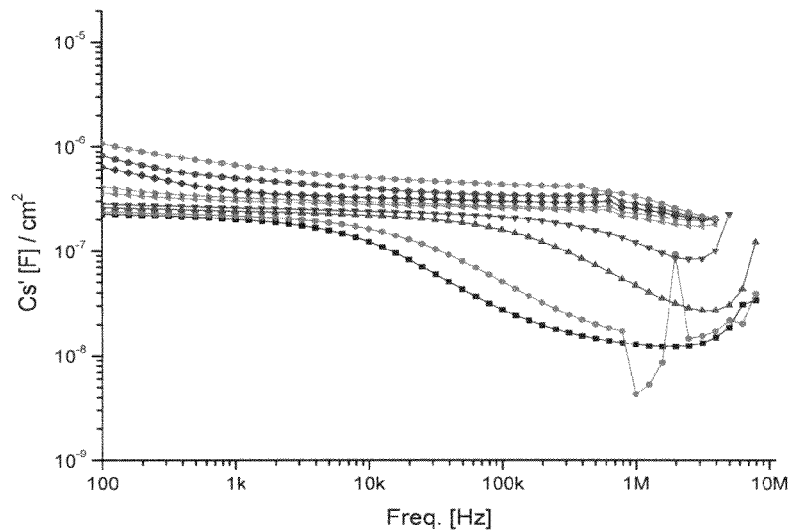

With reference to the impedance characteristics described in FIGS. 4a, 4b and 5, FIG. 9 illustrates the real part of the real part Zs' of the impedance of the moisture active element as described with reference to FIG. 6, FIG. 10 illustrates the imaginare part Zs", FIG. 11 illustrates the phase shift Phi as a function of frequency for different relative humidity levels (RH), and FIG. 12 illustrates the effective capacitance Cs' (F/cm²).

Example 3

Figure 13A:
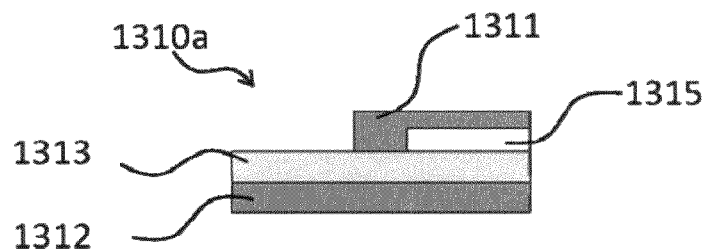
FIGS. 13a and 13b schematically illustrate embodiments of the moisture active element.
Figure 13B:
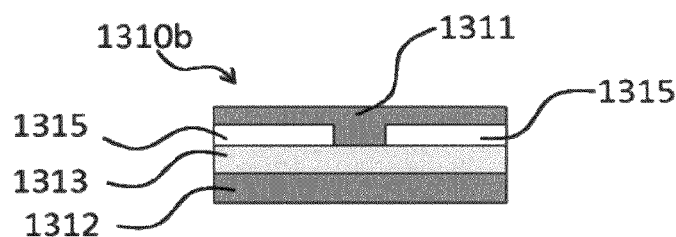

FIGS. 13a and 13b illustrate further embodiments of moisture active elements 1310a and 1310b formed by e.g. printing techniques, such as screen printing. The moisture active elements 1310a and 1310b each comprises a first inert electrode 1311 comprising, or formed of, carbon, and a second inert electrode 1312 of an aluminum foil. A hygroscopic, humidity sensitive, electrolyte layer 1313 is arranged between the first and second electrodes 1311, 1312. For example, the electrolyte layer 1313 comprises Poly(styrene sulfonic acid) sodium salt, PSSNa (M.W 500,000). As further illustrated, a lacquer layer 1315, intended for insulating and/or protecting, may be arranged between the electrolyte 1315 and the first carbon electrode 1311.

The electrolyte layer 1313 may be formed by deposition of electrolyte paste comprising de-ionized water and isopropanol solvent onto the aluminum electrode 1312. After evaporating the solvent in the electrolyte paste, the lacquer layer 1315 is printed on a portion of the electrolyte layer 1313, after which the lacquer layer is UV-cured.

The electrolyte layer 1313 of the moisture active element 1310a comprises an open area, which is not covered by the lacquer layer 1315, and which may be utilized as an effective area of the moisture active element 1310*a* wherein the carbon electrode 1311 is deposited such that a portion of the effective area is covered. In other words, the effective area of the moisture active element may defined by an opening in lacquer layer, which restricts and controls the absorption of e.g. water vapor. Hence, the sensitivity of the sensor may be controlled. The deposited carbon electrode 1311 may further be dried in a dryer.

The lacquer layer 1315 facilitates the manufacturing of the moisture sensor, wherein the moisture active element may be integrated with the antenna to form the moisture sensor device. The lacquer layer 1315 may further be arranged to define the contact area between the first electrode 1311 and the electrolyte layer 1313, as illustrated in FIG. 13*b*.

Example 4

FIG. 14*a* schematically illustrates manufacturing steps of an integrated printed moisture sensor tag 140, shown in FIG. 14*b*, according to an embodiment of the present invention. The moisture sensor tag 140 comprises a printed electrolyte based moisture active element which is integrated by screen printing into a resonant circuit also produced by screen printing.

With reference to FIG. 14*a*, a first step 141 comprises fabricating an antenna and bottom electrode for the sensor and additional capacitors. For example, an Al antenna is patterned on a plastic foil. A second step 142 comprises screen printing the solid electrolyte, most especially PSSNa (see Example 2). A third step 143 comprises screen printing of a protection layer, such as a lacquer layer, onto the parts of the Al bottom pattern. The protection layer plays three key roles: defining active area for sensor head; preventing electrical short between antenna or bottom electrode and a top electrode of the sensor or an electrical bridge to connect to the other edge of the antenna; and using as a dielectric for a additional printed capacitors in the resonant circuit. Extra capacitors may be used for defining the frequency band for the resonance frequency of the integrated moisture sensor. UV-cured lacquer paste is recommended due to its good compatibility with other layers, such as 5018 UV Curable Dielectric from DuPont and UVIVID SCREEN CN-CN00A from Sericol.

In FIG. 15, an exemplifying result for the integrated moiser sensor 140 in the form of the resonant frequency shift of about 30 kHz from very dry condition to very wet condition, is shown.

The invention has mainly been described above with reference to a number of explicitly disclosed embodiments. However, as is readily appreciated by a person skilled in the art, other embodiments than the ones disclosed above are equally possible within the scope of the invention, as defined by the appended patent claims.

What is claimed is:

1. A moisture sensor for measuring moisture in a building, comprising:
    a flexible carrier for attaching said sensor to a floor or inner wall of a building;
    a resonant circuit printed on said carrier;
    a first antenna printed on said carrier, arranged to receive an electromagnetic signal within a first frequency range of 9 kHz to 11 MHz to convert said signal into an AC voltage, the AC voltage being arranged to alternate within said first frequency range; and to feed said voltage to said resonant circuit,
    said first antenna being further arranged to emit an electromagnetic signal indicative of an impedance of said resonant circuit; and
    an encapsulation layer sealing said moisture sensor, the encapsulation layer comprising a humidity permeable portion;
    wherein said resonant circuit comprises a moisture reactive element comprising: a first and a second inert electrode comprising electrochemically substantially inert material, each electrode being arranged as a layer, and
    a hygroscopic solid electrolyte arranged as a layer and spatially between said first and second inert electrodes, the hygroscopic solid electrolyte, at least in the presence of moisture, forming mobile ions selected from a group consisting of cations and anions, and the hygroscopic solid electrolyte providing a complex impedance at least in response to said alternating voltage being applied across said first and second inert electrodes.

2. A sensor according to claim 1, wherein said hygroscopic solid electrolyte is sandwiched between said first and second inert electrodes.

3. A sensor according to claim 2, wherein the interface between said hygroscopic solid electrolyte and a respective one of said first and second inert electrodes is relatively smaller than the surface area of said hygroscopic solid electrolyte.

4. A sensor according to claim 1, wherein the interface between said hygroscopic solid electrolyte and a respective one of said first and second inert electrodes is relatively smaller than the surface area of said hygroscopic solid electrolyte.

5. A sensor according to claim 1, wherein at least one of said first and second inert electrodes is provided with apertures.

6. A sensor according to claim 1, wherein said first and second inert electrodes are in direct electrical contact with said hygroscopic solid electrolyte.

7. A sensor according to claim 1, wherein said mobile ions are mobile at least in response to at least one frequency within said first frequency range.

8. A sensor according to claim 1, wherein said resonant circuit and said antenna are both arranged on the same side of said carrier.

9. A sensor according to claim 1, wherein said circuit is a passive resonant circuit.

10. A sensor according to claim 1, wherein said hygroscopic solid electrolyte, at least in the presence of moisture, further forms immobile ions selected from a group consisting of polycations and polyanions.

11. A system comprising:
    a moisture sensor according to claim 1, and
    a reader comprising:
        a signal generator for generating and emitting an electromagnetic signal sweeping from a first to a second frequency within said first frequency range;
        a circuit arranged to receive a electromagnetic signal from said moisture sensor; and
        a converter arranged to convert said received electromagnetic signal to a value indicative of the presence of moisture in said moisture sensor.

12. A system according to claim 11, wherein the electromagnetic signal emitted by said reader is coupled into said first sensor by way of a magnetic coupling.

13. A system comprising:
    a first and second sensor according to claim 1, the second sensor including an electrolyte moisture level and being sealed with a moisture impervious seal to maintain the said electrolyte moisture level; and a reader comprising:

a generator for generating and emitting an electromagnetic signal having a first frequency; and an electric circuit comprising:

an antenna device arranged to receive a first reflected impedance from said first sensor and a second reflected impedance said second sensor, respectively; and a comparison device arranged to compare said first impedance to second impedance and to determine the moisture level of said first sensor based on the result of the comparison of said first and second moisture levels.

14. A system according to claim 13, wherein the electromagnetic signal emitted by said reader is coupled into said first sensor by way of a magnetic coupling.

15. A building structure, the structure being selected from a group consisting of walls, floors and ceilings, comprising: a moisture sensor according to claim 1, wherein said moisture sensor is arranged beneath a surface of said building structure to measure the humidity therein.

16. A method of producing a moisture sensor according to claim 1, comprising:

providing the flexible carrier;

printing the first antenna and the resonant circuitry on said flexible carrier;

providing the first electrode on said flexible substrate;

printing the layer of hygroscopic electrolyte on said first electrode; and providing the second electrode on said layer of hygroscopic electrolyte.

17. A method according to claim 16, wherein said first and second electrode are provided by means of printing.

18. A method according to claim 17, further comprising providing a lacquer layer.

19. A method according to claim 16, further comprising providing a lacquer layer.

20. A method for using a moisture sensor according to claim 1, comprising:

measuring moisture in a building using the moisture sensor.

* * * * *